United States Patent [19]
Kautzer et al.

[11] Patent Number: 6,149,301
[45] Date of Patent: Nov. 21, 2000

[54] X-RAY TARGET CENTERING APPARATUS FOR RADIOGRAPHIC IMAGING SYSTEM

[75] Inventors: Jeffrey Alan Kautzer, Waukesha, Wis.; Richard Aufrichtig, Mountain View, Calif.

[73] Assignee: General Electric Company, Milwaukee, Wis.

[21] Appl. No.: 09/224,241

[22] Filed: Dec. 30, 1998

[51] Int. Cl.[7] ................................................. A61B 6/08
[52] U.S. Cl. ............................................ 378/205; 378/157
[58] Field of Search ............................ 378/205, 206, 378/207, 204, 145, 147, 150, 157, 152

[56] References Cited

U.S. PATENT DOCUMENTS

| | | | |
|---|---|---|---|
| 3,502,878 | 3/1970 | Stewart et al. | 378/152 X |
| 4,618,980 | 10/1986 | Lescrenier et al. | 378/206 |
| 4,766,603 | 8/1988 | Okabe et al. | 378/152 |

*Primary Examiner*—David P. Porta
*Attorney, Agent, or Firm*—Craig A. Fieschko, Esq.; DeWitt Ross & Stevens S.C.; Phyllis Y. Price

[57] ABSTRACT

An apparatus for properly centering and/or collimating an X-ray beam with respect to a target to be radiographically imaged. A field definer is situated between an X-ray source and an X-ray detector at the location where the target is to be situated. The field definer includes a pair of stops between which the target may be located, and the stops may be horizontally relocated relative to each other to be placed in abutment with the target. A sensor in communication with the stops produces a signal dependent on the distance between the stops, and a controller utilizes this signal to adjust the X-ray source to emit radiation in a desired area with respect to the field between the stops. As an example, a target may be situated between the stops, the stops may be adjusted in abutment with the target, and the X-ray source will then be collimated to emit a radiation beam which is incident only on the target between the stops.

19 Claims, 1 Drawing Sheet

X-RAY TARGET CENTERING APPARATUS FOR RADIOGRAPHIC IMAGING SYSTEM

FIELD OF THE INVENTION

This disclosure concerns an invention relating generally to radiographic imaging systems, and more specifically to apparata and methods for properly locating targets to be imaged within such systems.

BACKGROUND OF THE INVENTION

The classic radiograph or "X-ray" image is obtained by situating a target to be imaged between an X-ray source and an X-ray detector made of photographic film. Emitted X-rays pass through the target to expose the film, and the degree of exposure at the various points on the film are largely determined by the density of the target along the path of the X-rays.

It is now common to utilize solid-state digital X-ray detectors, e.g., an array of switching elements and photodiodes, in place of film detectors. The charges generated by the X-rays on the various points of the detector are read and processed to generate a digital image of the target in electronic form, rather than an analog image on photographic film. Digital imaging is advantageous because the image can later be electronically transmitted to other locations, subjected to diagnostic algorithms to determine properties of the imaged target, and so on.

In both analog and digital radiographic imaging systems, there is commonly a need to properly position the target relative to the X-ray source and the X-ray detector. This is particularly true for cases where the physical dimensions of the target approach the dimensions of the X-ray detector. For the sake of efficiency, it is desirable to center the imaging apparatus so that the image is centered about the area of interest on the target, and it is also desirable to collimate the emitted radiation to cover only so much area on the target and its surroundings as necessary. This is particularly true in the case of digital imagers, wherein uncollimated radiation which misses the target may strike the detector to saturate it. This can potentially disable the digital detector for extended periods of time.

In order to overcome the aforementioned problems, centering of the target is generally accomplished by the use of a light source on the X-ray source. The light source is collimated to project a beam of light which is generally coincident with the radiation beam. Thus, a technician may adjust the location of the target within the light beam, and/or collimate the radiation and light beams with respect to the target, so as to center the target as desired. However, targeting errors may still occur owing to difficulties in determining the light beam's precise boundaries, and similar factors. There is thus a need for improved targeting apparata and methods.

SUMMARY OF THE INVENTION

The invention, which is defined by the claims set out at the end of this disclosure, is directed to a field definer for a radiographic imaging system. The field definer adjusts the radiation beam provided by an X-ray source to fall within a desired field about a target to be imaged. In preferred embodiments of the invention, the field definer includes a pair of stops wherein at least one stop is horizontally repositionable with respect to the other stop. The stops may thereby be positioned on opposing sides of the target. These stops may be provided on horizontally-oriented arms wherein at least one arm is movable with respect to the other to reposition its stop with respect to the stop on the other arm. A sensor which generates a signal dependent on the distance between the stops is then provided adjacent at least one of the arms. This sensor may be provided in the form of a rotating member which engages at least one of the arms, e.g., a toothed sprocket, wherein the sensor signal is dependent on the rotation of the rotating member. The X-ray source then collimates the radiation beam in accordance with the sensor signal to provide X-rays across a target field centered between the stops, with this target field having a size dependent on the sensor signal. Thus, as an example, the field definer may be situated between an X-ray source and an X-ray detector, and a target may be situated between its stops. The X-ray source will be collimated to project X-rays onto a desired field about the target, whose horizontal boundaries are delimited by the stops. Further advantages, features, and objects of the invention will be apparent from the following detailed description of the invention in conjunction with the associated drawings.

Detailed Description of Preferred Embodiments of the Invention

Figure 1:
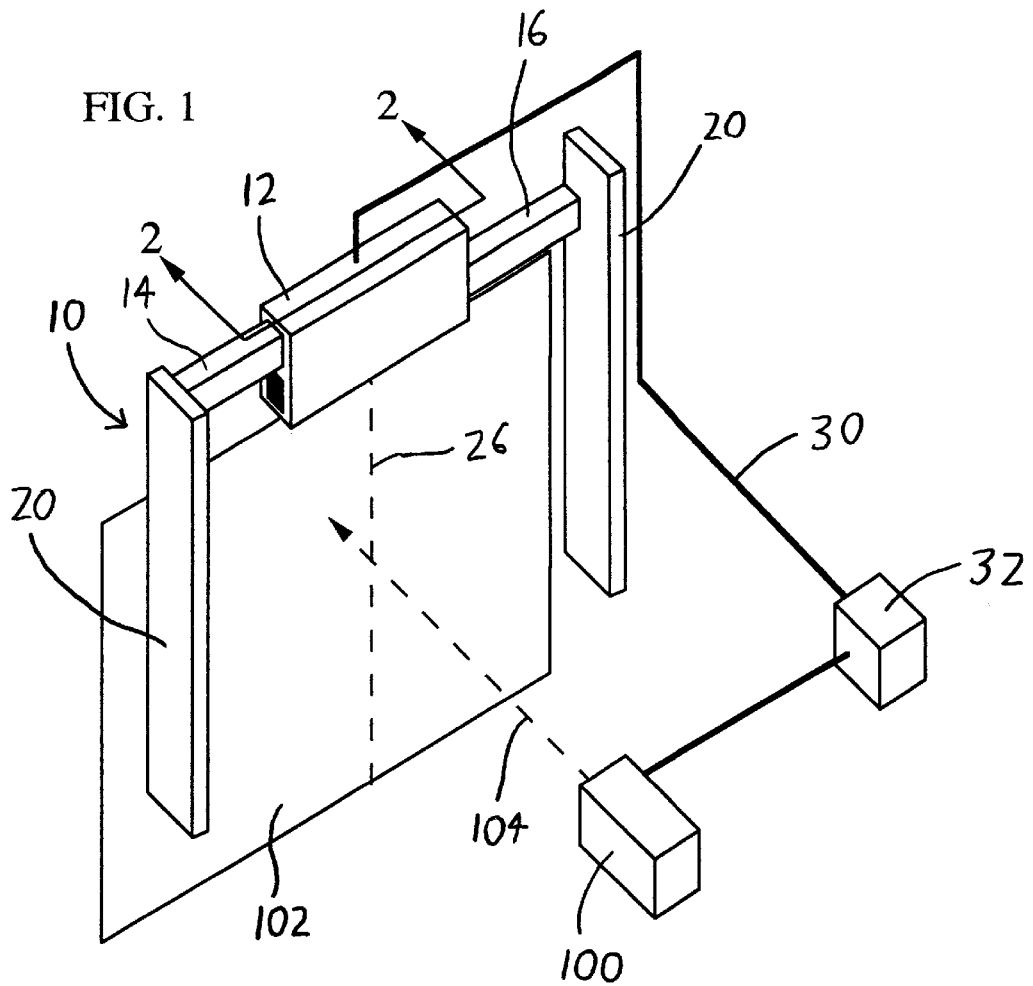
FIG. 1 is a perspective view of a basic embodiment of the apparatus of the invention.

Reference is now made to the drawings, wherein an exemplary version of the invention is illustrated to assist the reader's understanding. In FIG. 1, a portion of an X-ray source (e.g., a collimator on an X-ray tube) is illustrated at 100, and its X-ray detector is illustrated at 102. When radiographic imaging is performed, a target (not shown in the Figures) is situated between the source 100 and the detector 102, usually closely adjacent the detector 102, so that the radiation beam delivered by the source 100 intersects the target and is collected by the detector 102. The radiation beam is represented in FIG. 1 by the phantom line 104, which is located at the geometric center of the radiation beam.

As noted above, it is desirable to properly center a target with respect to ray 104 during imaging so that only the areas of interest within the target are imaged, and so that the radiation dose delivered to the target is no greater than necessary. Further, in digital imaging, where the target is a human body—e.g., where a chest X-ray is being taken—it is particularly important that the target be centered horizontally within the beam, since such horizontal offsets are more likely to result in "raw" radiation striking the detector 102 and saturating it. Since the human body is generally taller than it is wide, vertical offset errors are less likely to result in the radiation beam falling on the detector 102.

Figure 2:
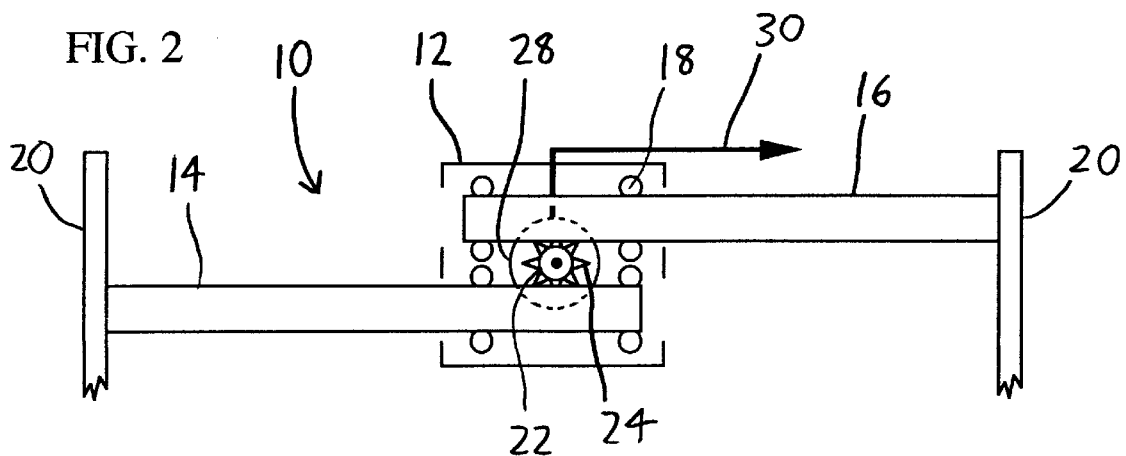
FIG. 2 is a partial front elevational view of the apparatus of FIG. 1, shown with the housing 12 of the field definer 10 sectioned along the line 2—2 of FIG. 1.

FIGS. 1 and 2 then illustrate a field definer 10, which includes a housing 12 from which a pair of arms 14 and 16 extend. The housing 12 is preferably situated on the wall or other support whereupon the detector 102 is situated so that the arms 14 and 16 are aligned in planes between the source 100 and the detector 102. Additionally, the housing 12 is preferably situated slightly above the detector 102 (as shown in FIG. 1), or otherwise substantially out of the path of the radiation beam, so that it (and also preferably the arms 14/16) does not cause scatter in the radiation beam and/or otherwise interfere with the image. Thus, as an alternative to the arrangement shown in FIG. 1, the housing 12 and its arms 14/16 could instead be situated below the detector 102 and under the path of the radiation beam. However, if desired, the housing 12 could rest within the path of the radiation beam so long as it would not unacceptably interfere with imaging.

Referring primarily to FIG. 2, within the housing 12, the arms 14 and 16 are slidably mounted on bearings 18 (or other supports allowing motion of the arms 14 and 16) to allow horizontal extension and retraction in planes which are generally parallel to the area of the detector 102. The arms 14 and 16 each terminate in stops 20 which preferably protrude outwardly from the planes wherein the arms 14 and 16 travel so that a target may be located between these stops 20. In the case where the field definer 10 is situated above the detector 102 (as in the Figures, rather than being situated below or to its side), the stops 20 also extend downwardly to allow a target to rest therebetween.

As best illustrated in FIG. 2, a rotating member 22 is situated between the arms 14 and 16 to bear against them, thereby linking the arms 14 and 16 to extend and retract in opposing fashion. Thus, when one stop 20 is moved horizontally inwardly or outwardly, the other stop 20 does as well. While the rotating member 22 may take the form of a simple wheel which rolls against the arms 14 and 16, it preferably includes structure which positively engages the arms 14 and 16 to link them together in coactuating fashion; thus, the rotating member 22 is preferably provided in the form of a sprocket or gear which bears teeth 24 engaging the arms. As a result, if a target such as a human body is situated between the stops 20, pushing one stop 20 inwardly to abut the body will cause the other stop 20 to also move inwardly towards the target. The stops 20 and/or the target may be moved until both stops 20 rest in abutment with the opposing sides of the target. For reasons which will be discussed at greater length below, the rotating member 22 is preferably horizontally centered so that the arms 14 and 16 are linked to move symmetrically about and equidistantly from an axis 26 (shown in FIG. 1) which intersects the horizontal center of the radiation beam 104.

As also shown in FIG. 2, the rotating member 22 is then linked to a sensor 28 which generates a sensor signal which is dependent on the rotation of the rotating member 22, and therefore to the horizontal location of the arms 14 and 16 with respect to the axis 26. The sensor 28 may take a variety of forms, e.g., a potentiometer, a rotary shaft encoder, a shaft pickup in communication with a pulse counter, etc.

The signal from sensor 28 is provided along line 30 to a controller 32, which is in turn connected to the X-ray source 100. The controller 32 utilizes the signal from sensor 28 to adjust the source 100 so that the radiation field of the source 100 rests within the stops 20 of the field definer 10. If the source-to-image distance (the SID, i.e., the distance from the source 100 to the detector 102) is fixed, the relationship between the width of the field definer stops 20 and the width of the collimated radiation field is well-defined, and the radiation field can be centered between the stops 20 by simply adjusting the collimation of the source 100. However, if the SID is variable (i.e., if the distance between the source 100 and the detector 102 is variable), either or both of the SID and the collimation can be varied in order to center the radiation field between the stops. The sensor 28 and controller 32 can be provided in analog or digital form. In the case of a digital imaging system, the controller 32 may be provided within (or in conjunction with) the processors provided for image processing, or it could instead be provided separately.

As a result of the foregoing arrangement, when the stops 20 are situated in abutment with a target, the source 100 is adjusted to provide a radiation beam which is centered about the target, and wherein its boundaries are coincident with those of the target.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. Following is an exemplary list of such modifications.

First, while the description above notes that the radiation beam is collimated to project between the stops 20 to cover the horizontal extent of the target, the controller 32 and/or source 100 could instead be adjusted so that the radiation beam has some other relation with respect to the stops 20 (e.g., it may rest slightly within the stops 20, slightly outside the stops 20, etc.).

Second, the sensor 28 need not be provided in the form of a rotary displacement sensor which is linked to the rotating member 22 and which senses rotation, and it could instead detect linear displacement. As an example, the sensor 28 could be coupled to one or both of the arms 14 and 16 to detect their horizontal motion. There are numerous ways to provide such an arrangement, e.g., inductive proximity sensors which detect structure formed on one or more of the arms 14 and 16, optical sensors which detect apertures, or other optically distinct areas on the arms, etc.

Third, while the arms 14 and 16 are described as moving symmetrically and equidistantly about the horizontal center of the radiation field (depicted by phantom line 26), it is also possible to provide one arm in a fixed position with respect to the detector and have only the other arm move. In this case, the sensor would provide a signal dependent on the displacement of the moving arm/stop, and the immobile arm could simply be provided as a portion of the housing and/or the support structure for the detector. Unlike the embodiment shown in FIGS. 1 and 2, the center of the field between the stops would be mobile. Therefore, the collimator must take account of this condition and only allow expansion or reduction of the projected radiation beam in an area to one side of the immobile stop. Alternatively, the source 100 could be mounted on a linear actuator which receives feedback from the controller 32 and carries the source 100 horizontally so that its beam is always centered between the stops.

The invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A radiographic imaging system comprising:
   a. a pair of stops, at least one stop being horizontally repositionable with respect to the other stop, wherein the stops have a space defined therebetween, whereby an X-ray target may be situated between the stops;
   b. a sensor providing a sensor signal dependent on the distance between the stops;
   c. an X-ray source providing X-rays across a target field having a field size dependent on the sensor signal.

2. The radiographic imaging system of claim 1 further comprising a pair of parallel arms, each arm having one of the stops situated thereon.

3. The radiographic imaging system of claim 2 further comprising a rotating member situated between the arms.

4. The radiographic imaging system of claim 3 wherein the rotating member bears teeth engaging the arms.

5. The radiographic imaging system of claim 3 wherein the sensor signal is dependent on the rotation of the rotating member.

6. The radiographic imaging system of claim 1 wherein the target field is situated between the stops.

7. The radiographic imaging system of claim 1 further comprising an X-ray detector, with the stops being located between the X-ray source and X-ray detector.

8. A radiographic imaging system comprising:
   a. a pair of arms linked to horizontally move in opposing fashion, the arms having stops defined thereon,
   b. a sensor situated adjacent at least one of the arms, the sensor providing a sensor signal dependent on the horizontal location of at least one of the arms,
   c. an X-ray source in communication with the sensor and receiving the sensor signal therefrom, the X-ray source providing X-rays across a target field having a size dependent on the sensor signals,
   d. an X-ray detector, with the stops being located between the X-ray source and X-ray detector.

9. The radiographic imaging system of claim 8 further comprising a rotating member engaging at least one of the arms.

10. The radiographic imaging system of claim 9 wherein the rotating member bears teeth engaging at least one of the arms.

11. The radiographic imaging system of claim 9 wherein the sensor signal is dependent on the rotation of the rotating member.

12. The radiographic imaging system of claim 8 wherein the arms are situated in substantially common planes, and wherein the stops protrude outwardly from these planes.

13. The radiographic imaging system of claim 8 wherein the stops have a space defined therebetween, whereby an X-ray target may be situated within the space.

14. A radiographic imaging system comprising:
   a. an X-ray source,
   b. an X-ray detector,
   c. a field definer situated between the X-ray source and X-ray detector, the field definer including:
      (1) a pair of horizontally-spaced stops, the stops being linked to horizontally move in opposing fashion,
      (2) a sensor in signal communication with the X-ray source, the signal being dependent on the horizontal position of at least one of the stops.

15. The radiographic imaging system of claim 14 wherein:
   the X-ray source includes an X-ray collimator, and
   the sensor is in signal communication with the X-ray collimator, whereby X-rays emitted by the X-ray source are collimated by the X-ray collimator to be received in a target field defined between the stops.

16. The radiographic imaging system of claim 14 further comprising a pair of parallel arms, each arm having one of the stops situated thereon.

17. The radiographic imaging system of claim 16 further comprising a rotating member engaging the arms.

18. The radiographic imaging system of claim 17 wherein the sensor signal is dependent on the rotation of the rotating member.

19. The radiographic imaging system of claim 14 wherein the stops have a space defined therebetween, whereby an X-ray target may be situated between the stops.

\* \* \* \* \*